United States Patent
Kemmochi et al.

(10) Patent No.: US 12,105,042 B2
(45) Date of Patent: Oct. 1, 2024

(54) METHOD AND SYSTEM FOR MEASURING CONDUCTIVITY OF DECATIONIZED WATER

(71) Applicant: ORGANO CORPORATION, Tokyo (JP)

(72) Inventors: Chika Kemmochi, Tokyo (JP); Koji Yamanaka, Tokyo (JP)

(73) Assignee: ORGANO CORPORATION, Tokyo (JP)

( * ) Notice: Subject to any disclaimer, the term of this patent is extended or adjusted under 35 U.S.C. 154(b) by 916 days.

(21) Appl. No.: 16/648,869

(22) PCT Filed: Aug. 2, 2018

(86) PCT No.: PCT/JP2018/029092
§ 371 (c)(1),
(2) Date: Mar. 19, 2020

(87) PCT Pub. No.: WO2019/058779
PCT Pub. Date: Mar. 28, 2019

(65) Prior Publication Data
US 2020/0284742 A1    Sep. 10, 2020

(30) Foreign Application Priority Data
Sep. 25, 2017  (JP) .................. 2017-183386

(51) Int. Cl.
*C02F 1/469*     (2023.01)
*G01N 27/10*    (2006.01)
(Continued)

(52) U.S. Cl.
CPC ............. *G01N 27/10* (2013.01); *C02F 1/469* (2013.01); *C02F 1/4695* (2013.01);
(Continued)

(58) Field of Classification Search
CPC ............... G01N 27/10; G01N 33/0018; G01N 33/182; B01D 61/48; B01D 61/54;
(Continued)

(56) References Cited

U.S. PATENT DOCUMENTS 4,804,451 A * 2/1989 Palmer ................ B01D 61/48
                                                                204/633
5,788,828 A    8/1998 Nakatsu et al.
(Continued)

FOREIGN PATENT DOCUMENTS

JP    8-332482    12/1996
JP    9-57271     3/1997
(Continued)

OTHER PUBLICATIONS

Official Communication issued in International Bureau of WIPO Patent Application No. PCT/JP2018/029092, dated Oct. 30, 2018.
Office Action issued in corresponding Taiwanese Patent Application No. 107132723 dated Jul. 4, 2022, along with English translation thereof.

*Primary Examiner* — Zulmariam Mendez
(74) *Attorney, Agent, or Firm* — Greenblum & Bernstein, P.L.C.

(57) ABSTRACT

Time until a conductivity meter is ready to measure a conductivity after an electric decationizing apparatus starts is shortened.
Water to be treated that contains cations and anions is supplied to the electric decationizing apparatus while applying a first voltage to the electric decationizing apparatus, and decationized water is generated. Next, the decationized water that is generated by the electric decationizing apparatus is supplied to the conductivity meter in order to measure conductivity of the decationized water. Before the first voltage is applied to the electric decationizing apparatus and before the conductivity meter begins measuring the conductivity of the decationized water, a second voltage that
(Continued)

is lower than the first voltage is applied to the electric decationizing apparatus in a state in which the electric decationizing apparatus is charged with water to be treated.

5 Claims, 4 Drawing Sheets

(51) Int. Cl.
  *G01N 33/00* (2006.01)
  *G01N 33/18* (2006.01)
(52) U.S. Cl.
  CPC ..... *G01N 33/0018* (2013.01); *G01N 33/1813* (2013.01); *G01N 33/182* (2013.01); *C02F 2201/4612* (2013.01); *C02F 2201/46125* (2013.01); *C02F 2209/05* (2013.01)
(58) Field of Classification Search
  CPC ............... C02F 1/469; C02F 1/4695; C02F 2201/4612; C02F 2201/46125; C02F 2209/05
  See application file for complete search history.

(56) References Cited

U.S. PATENT DOCUMENTS

| | | | | |
|---|---|---|---|---|
| 2008/0308482 | A1* | 12/2008 | Tajima | ............ B01J 47/08 210/243 |
| 2012/0178175 | A1 | 7/2012 | Crosman | |

FOREIGN PATENT DOCUMENTS

| | | | | |
|---|---|---|---|---|
| JP | H07-236090 | * | 3/1997 | ............ B01D 61/48 |
| JP | 9-210943 | | 8/1997 | |
| JP | 11-57420 | | 3/1999 | |
| JP | 2000-28107 | | 1/2000 | |
| JP | 2001-141596 | | 5/2001 | |
| JP | 2004-033977 | A | 2/2004 | |
| JP | 3704289 | | 10/2005 | |
| JP | 2010-99594 | | 5/2010 | |
| JP | 4671272 | | 4/2011 | |
| JP | 2012-228674 | | 11/2012 | |
| JP | 2013-52354 | | 3/2013 | |

* cited by examiner

METHOD AND SYSTEM FOR MEASURING CONDUCTIVITY OF DECATIONIZED WATER

TECHNICAL FIELD

The present application is based upon and claims priority from Japanese Patent Application No. 2017-183386 filed on Sep. 25, 2017, the disclosure of which is hereby incorporated by reference herein in its entirety.

The present invention is related to a method and system for measuring conductivity of decationized water, particularly to a method of measuring the conductivity of condensate water in a thermal power plant.

BACKGROUND ART

A water circulation operation is conducted in a thermal power plant. That is, high temperature and high pressure steam is generated in a boiler, and is introduced into a steam turbine. The steam that is discharged from the steam turbine is condensed into condensate water in a condenser, and the condensate water is fed to the boiler as feed water. Since impurities, such as corrosion products, accumulate in the condensate water, a thermal power plant is provided with a condensate demineralizer that removes the impurities from the condensate water during normal operation. When the condenser is cooled by sea water, the condensate demineralizer also works to protect the condensate water system by removing sodium chloride and the like for a short period, which is contained in sea water that may mix in the condensate water. However, if more than a predetermined amount of sea water flows in the condensate demineralizer, then the condensate demineralizer will exceed its operational limit. For this reason, a thermal power plant has a conductivity meter for the purpose of detecting sea water component in the condensate water.

On the other hand, in a thermal power plant, an operation of adding a pH adjuster, such as ammonia, to the condensate water to alkalify the condensate water is conducted in order to prevent piping etc. of the condensate water system from corroding. For this reason, the condensate water has low specific resistance and high conductivity, and the specific resistance and the conductivity do not largely change when a small amount of sea water mixes in the condensate water system. Therefore, it is difficult to accurately detect the mixing of sea water by means of a conductivity meter. In order to solve this problem, cations, such as ammonia, may be removed by an electric decationizing apparatus in advance, and the condensate water, whose conductivity has been reduced, may be supplied to a conductivity meter (JP4671272, JP3704289). This method enhances the accuracy for detecting anions that come from sea water and makes it possible to detect the mixing of sea water more accurately.

SUMMARY OF INVENTION

In a thermal power plant, daily start and stop (DSS) operations and weekly start and stop (WSS) operations are conducted in order to cope with fluctuating load, and start and stop operations are frequently repeated in the thermal power plant. The electric decationizing apparatus operates while the thermal power plant is in operation, but when the operation stops, the operation of the electric decationizing apparatus also stops. Since no voltage is applied to the electric decationizing apparatus during stoppage, cations in the condensate water that remain in the electric decationizing apparatus diffuse in the electric decationizing apparatus. Accordingly, condensate water that contains a larger number of cations than the normal level may be discharged from the electric decationizing apparatus for a certain time after the electric decationizing apparatus restarts. In that case, highly conductive condensate water is supplied to the conductivity meter, and anions that come from sea water cannot be accurately detected. Although this state disappears after a while, the conductivity meter must wait until it is ready for measurement.

The present invention aims at providing a method and a system for measuring the conductivity of decationized water that can, after the electric decationizing apparatus starts, shorten the amount of time that is needed for the conductivity meter to begin measuring the conductivity.

According to an aspect of the present invention, a method of measuring conductivity of decationized water comprises the steps of: supplying water to be treated that contains cations and anions to an electric decationizing apparatus while applying a first voltage to the electric decationizing apparatus, and generating decationized water; supplying the decationized water that is generated by the electric decationizing apparatus to a conductivity meter in order to measure conductivity of the decationized water; and before the first voltage is applied to the electric decationizing apparatus and before the conductivity meter begins measuring the conductivity of the decationized water, applying a second voltage that is lower than the first voltage to the electric decationizing apparatus in a state in which the electric decationizing apparatus is charged with water to be treated. Furthermore, a system for measuring conductivity of decationized water comprises a control that controls the electric decationizing apparatus in this manner.

According to the present invention, it is possible to provide a method and a system for measuring conductivity of decationized water that can, after the electric decationizing apparatus starts, shorten the amount of time that is needed for the conductivity meter to begin measuring the conductivity.

The above-described and other objects, features, and advantages of this application will become apparent from the following detailed description with reference to the accompanying drawings that illustrate the present application.

| List of Reference Numerals | |
| --- | --- |
| 1, 101, 201 | System for measuring conductivity |
| 2 | Flow meter |
| 3, 3a, 3b | Electric decationizing apparatus |
| 4 | Conductivity meter |
| 5, 105, 205 | Control |
| 6 | Line |
| 7 | Valve |
| 8 | Condensate water line |
| 31 | Deionization chamber |
| 32, 33 | Condensation chamber |
| 38, 38a, 38b | Power supply |
| 39 | Cation exchanger |

DESCRIPTION OF EMBODIMENTS

Some embodiments of the present invention will be described with reference to the drawings. In each embodiment, water to be treated is condensate water of a thermal power plant. In other words, the system for measuring conductivity in each embodiment of the present invention is a system that a thermal power plant has. However, the present invention is not limited to this, and can be applied to a method and a system for measuring the conductivity of decationized water that is generated by an electric decationizing apparatus.

First Embodiment

Figure 1:
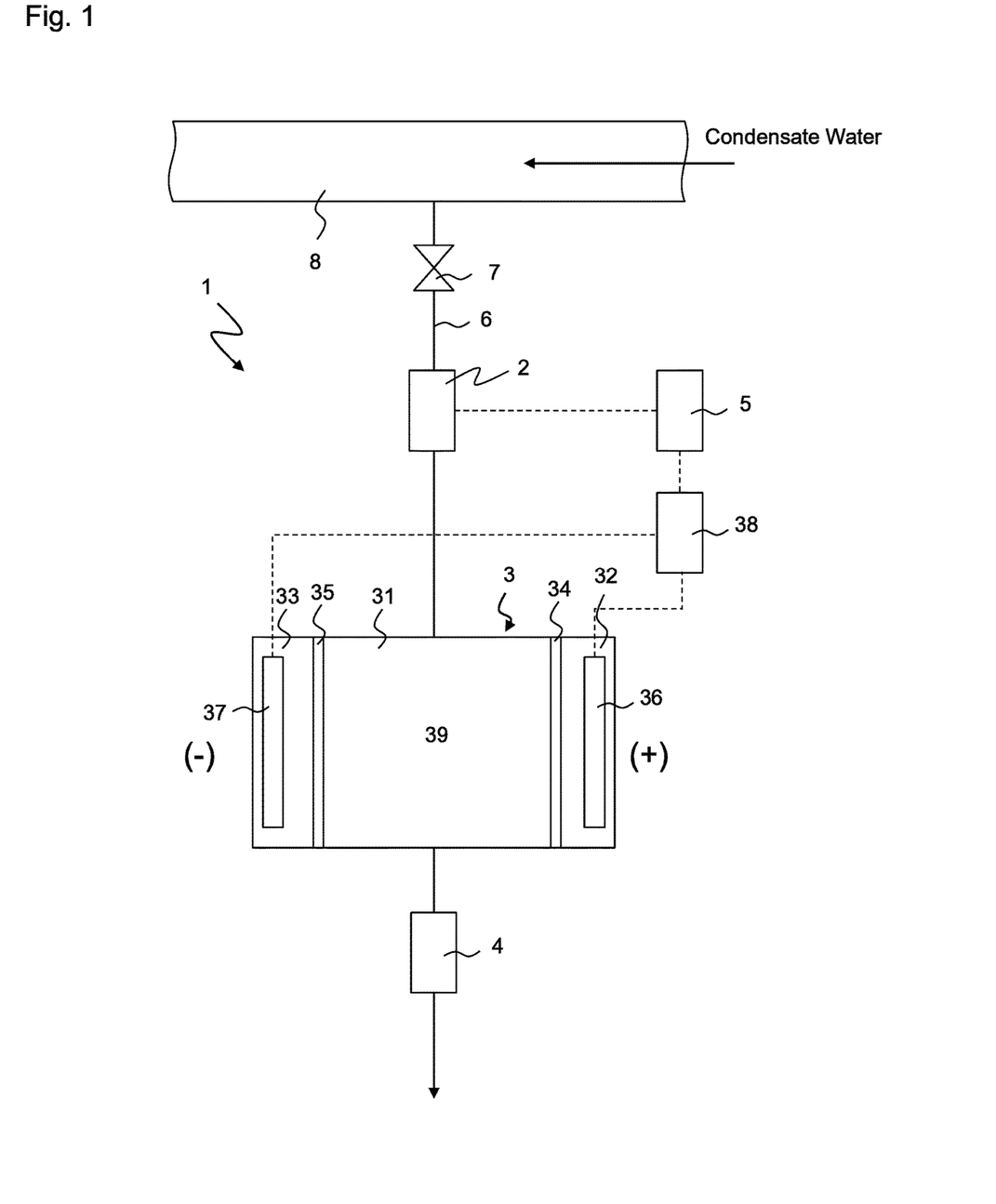
FIG. 1 is a conceptual view of a system for measuring the conductivity of decationized water according to the first embodiment of the present invention.

FIG. 1 shows a conceptual view of system for measuring the conductivity of decationized water 1 according to the first embodiment of the present invention (hereinafter referred to as system 1). System 1 has electric decationizing apparatus 3, conductivity meter 4, flow meter 2 and valve 7. These apparatuses are arranged on line 6 that branches from condensate water line 8. Electric decationizing apparatus 3 generates decationized water while applying first voltage V1 to water to be treated that contains cations and anions. First voltage V1 is, for example, 0.8V. Conductivity meter 4 measures the conductivity of decationized water that is generated by electric decationizing apparatus 3. Flow meter 2 measures the flow rate of the condensate water (water to be treated) that flows into electric decationizing apparatus 3. Valve 7 is normally opened, but is closed when system 1 has to be isolated from the condensate water system. Conductivity meter 4 is connected to a drain (not shown) at the downstream thereof, and the water is reused as condensate water or is disposed of.

Electric decationizing apparatus 3 has deionization chamber 31 and a pair of condensation chambers 32, 33 that are arranged on both sides of deionization chamber 31 via cation exchange membranes 34, 35. Positive electrode 36 is arranged in condensation chamber 32, and negative electrode 37 is arranged in condensation chamber 33, and condensation chambers 32, 33 also function as electrode chambers. Positive electrode 36 and negative electrode 37 are connected to DC power supply 38. Deionization chamber 31 is charged with cation exchanger 39. The arrangement of cation exchanger 39 is not limited as long as it can capture and remove cation components, but a cation exchange resin, a monolith type porous cation exchanger (hereinafter referred to simply as "monolith"), a fibrous porous cation exchanger and a particle aggregation type porous ion exchanger are preferably used.

Examples of monoliths include a monolith having an open cell structure having mesopores with an average diameter of 1-1000 μm, preferably 10-100 μm, formed in the wall of interconnected macropores, wherein the monolith has a total pore volume of 1-50 ml/g, preferably 4-20 ml/g, ion exchange groups that are evenly distributed and an ion exchanging capacity of 0.5 mg equivalent/g dry porous structure or more. Other characteristics of the monolith and the method of manufacturing the same are disclosed, for example, in JP 2003-334560.

A monolith that is used as the cation exchanger can largely increase pore volume and specific surface area. This is very advantageous because the deionizing efficiency of the electro decationizing apparatus is significantly improved. A monolith having a total pore volume that is less than 1 ml/g is not advantageous because the amount of water that passes through a unit sectional area is decreased and the treatment capacity is lowered. On the other hand, a total pore volume that exceeds 50 ml/g is not advantageous because the percentage of the skeleton is decreased and the porous structure is significantly weakened. It is preferable in terms of ensuring both the strength of the porous structure and good deionizing efficiency to use a monolith having a total pore volume of 1-50 ml/g as the ion exchanger of the electro decationizing apparatus. Furthermore, a monolith having an ion exchanging capacity that is less than 0.5 mg equivalent/g dry porous structure is not advantageous because the ion absorbing capacity is insufficient. In addition, the state in which ion exchange groups are unevenly distributed is not advantageous because this state makes the movement of ions uneven in the porous cation exchanger and prevents the ions that have been absorbed from being promptly removed.

Examples of fibrous porous ion exchangers include a monofilament or a woven or nonwoven fabric that are disclosed in JP5-64726, wherein the fabric is formed by a group of monofilaments, as well as an ion exchanger in which exchange groups are introduced into these products by radiation graft polymerization and that are formed in a certain shape. Examples of particle aggregation type porous ion exchangers include a mixed polymer of a thermoplastic polymer and a thermosetting polymer, disclosed, for example, in JP10-192716 and JP10-192717, as well as an ion exchanger in which ion exchange resin particles are combined by a cross-linked polymer and that are formed in a certain shape.

Electric decationizing apparatus 3 of the present embodiment is an electro deionizing apparatus (EDI). In the EDI, cation components ($NH_4^+$, $NA^+$, $CA^{2+}$, $Mg^{2+}$ and the like) are captured by cation exchanger 39, and at the same time, water dissociation reaction occurs in deionization chamber 31 such that hydrogen ions and hydroxide ions are generated. The cation components that have been captured by cation exchanger 39 are replaced with hydrogen ions and are released from cation exchanger 39. The cation components that have been released move along cation exchanger 39 to cation exchange membrane 35 on the side of negative electrode 37 by electrophoresis, are electrodialyzed by cation exchange membrane 35, and flow into condensation chamber 33. The cation components that have moved to condensation chamber 33 are discharged together with condensed water that flows in condensation chamber 33. Since the exchange groups of cation exchanger 39 release cation components after the exchange groups are combined with the cation components, and combine with hydrogen ions again, cation exchanger 39 is continuously regenerated. Since the removal of cation components and the regeneration of cation exchanger 39 occur automatically and continuously in the EDI in this manner, it is basically unnecessary to conduct the regeneration of cation exchanger 39 in a separate process. It should be noted that electric decationizing apparatus 3 is not limited to an EDI, and it may be an electrodialysis apparatus (ED) that is not charged with cation exchanger 39.

System 1 further has control 5 that controls electric decationizing apparatus 3. Control 5 is connected both to flow meter 2 and to power supply 38 of electric decationizing apparatus 3. Now, the method of operating system 1 and the function of control 5 will be described. Condensate water flows through condensate water line 8 during operation of the plant. Valve 7 is opened, and a part of the condensate water is introduced into electric decationizing apparatus 3 through line 6. The flow rate of the condensate water that flows through line 6, that is, the flow rate of water to be treated that is introduced into electric decationizing apparatus 3, is measured by flow meter 2 that is provided upstream of electric decationizing apparatus 3.

Condensate water (water to be treated) contains ammonia or hydrazine in order to prevent the corrosion of the piping and facilities of the condensate water system. These are pH adjusters that are added to the condensate water in order to adjust the pH of the condensate water. The pH of the condensate water has been set at about 8.5-9.8 in conventional thermal power plants, but may recently be set at 10 or more. The pH adjuster is normally present in the condensate water in the form of cations (cation components). For example, ammonia is present in the form of $NH_4^+$ in the condensate water. Cations in the water to be treated are captured by cation exchanger 39 of electric decationizing apparatus 3, and is discharged to condensation chamber 33 on the side of negative electrode 37 through cation exchange membrane 35. The treated water from which cation components are removed by electric decationizing apparatus 3 becomes substantially pure water. Thus, the conductivity of the treated water that is measured by conductivity meter 4 is around 0.06 µS/cm.

There is possibility that sea water intrudes into the condensate water system that is connected to a sea water cooling type condenser. Specifically, since the pressure of the condenser is low on the steam side, if a pin hole or the like is generated on the condenser tube in which sea water flows, then sea water intrudes into the steam side from the tube, and thereby significantly increases salt concentration in the condensate water. Salts that are contained in sea water include NaCl, $Na_2SO_4$ and the like. When the condensate water in which these salts are mixed is introduced into electric decationizing apparatus 3, cation exchanger 39 captures $NH_4^+$, $Na^+$ to allow treated water that contains HCl, $H_2SO_4$ and the like to be discharged from electric decationizing apparatus 3. Conductivity meter 4 detects anions that are present in the treated water in the form of $Cl^-$, $SO_4^{-2}$ and the like. Therefore, the conductivity that is measured by conductivity meter 4 is larger than the normal level (for example, 0.1 µS/cm or more). In this manner, it is possible to detect the intrusion of sea water into the condensate water by using conductivity meter 4 that measures the conductivity of the treated water that is free of most cations and that contains anions that come from sea water, such as chlorine ions. Such conductivity meter 4 is also called an acid conductivity meter.

Next, the operation of system 1 at a time when a thermal power plant restarts after it stopped will be described. When a thermal power plant stops, the flow of condensate water also stops, and the flow rate of the condensate water that is introduced into electric decationizing apparatus 3 also becomes zero. The output signal of flow meter 2 is transmitted to control 5, and control 5 judges that the flow rate is zero, that is, the thermal power plant has stopped. Control 5 controls power supply 38 in order to lower the voltage that is applied to positive electrode 36. Second voltage V2 that is lower than first voltage V1 is applied to positive electrode 36.

Figure 2A:
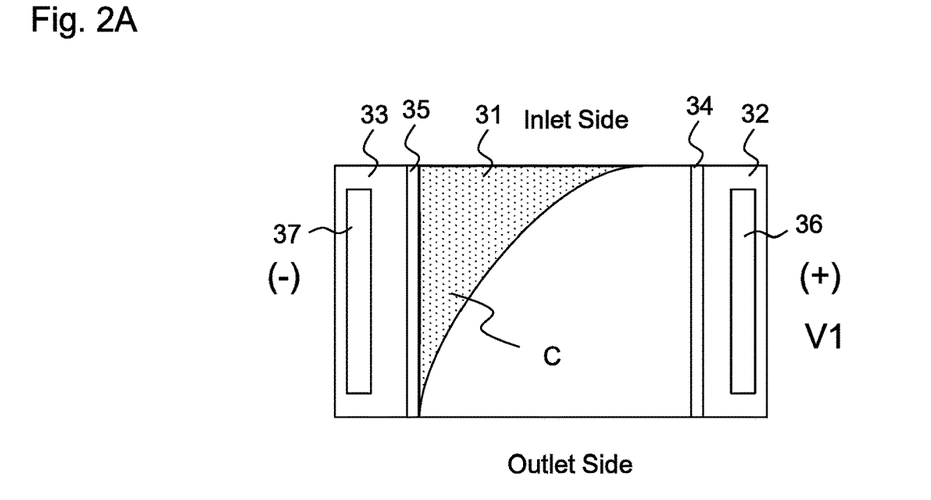
FIG. 2A is a conceptual view illustrating the distribution of cations in the deionization chamber before the operation of the plant stops according to the first embodiment and the comparative example.
Figure 2B:
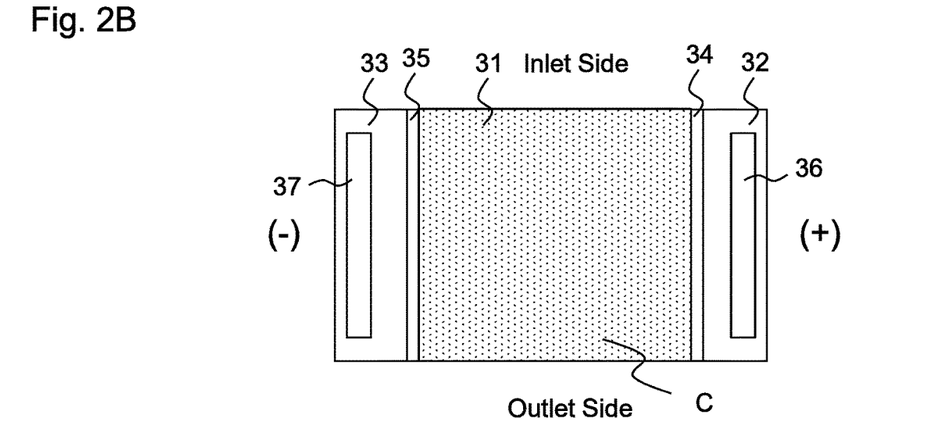
FIG. 2B is a conceptual view illustrating the distribution of cations in the deionization chamber after the operation of the plant stops according to the comparative example.
Figure 2C:
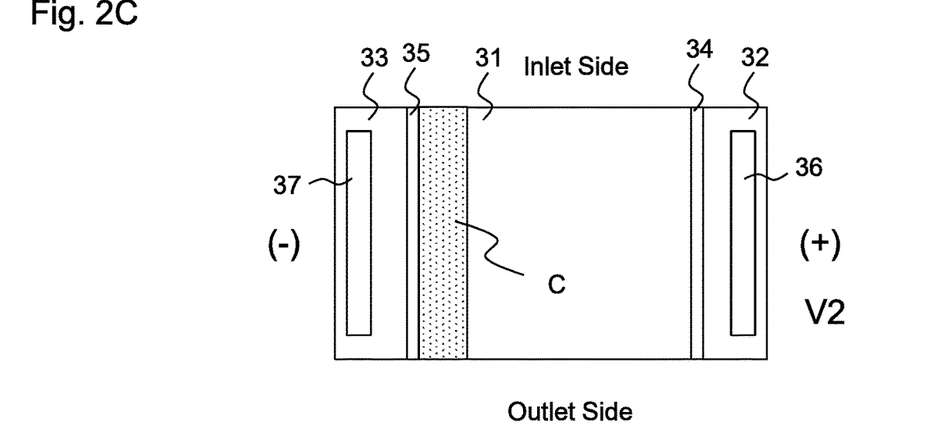
FIG. 2C is a conceptual view illustrating the distribution of cations in the deionization chamber after the operation of the plant stops according to the first embodiment.

FIGS. 2A-2C are conceptual views illustrating the distribution of cations C in deionization chamber 31 according to the present embodiment and a comparative example. The exchange groups of cation exchanger 39 in deionization chamber 31 holds cations, and the exchange groups are distributed on the side of negative electrode 37 before power supply 38 stops. Specifically, cations C are distributed on the side of negative electrode 37, as shown in FIG. 2A. This state is common both to the present embodiment and to the comparative example. No cation C is substantially present on the side of outlet of electric decationizing apparatus 3, and treated water that is discharged from electric decationizing apparatus 3 is decationized water that is free of cations. Although not illustrated, cations C are also present in condensation chamber 33. It should be noted that decationized water is not limited to water that is completely free of cations, but may contain a small number of cations.

In the comparative example, when control 5 judges that the flow rate of the condensate water that is introduced into electric decationizing apparatus 3 becomes zero, that is, the thermal power plant has stopped, control 5 deactivates power supply 38 in order to set the voltage between positive electrode 36 and negative electrode 37 of electric decationizing apparatus 3 at zero. Thereafter, cations C diffuse and are substantially evenly distributed in deionization chamber 31, as shown in FIG. 2B. A part of cations C in condensation chamber 33 also intrude into deionization chamber 31 through cation exchange membrane 35. Thereafter, when the thermal power plant restarts and electric decationizing apparatus 3 is activated, cations C are gradually distributed on the side of negative electrode 37, and the state shown in FIG. 2A is restored. Cations C that have intruded into deionization chamber 31 from condensation chamber 33 also flow back to condensation chamber 33 through cation exchange membrane 35.

On the other hand, according to the present embodiment, second voltage V2 that is smaller than first voltage V1 is applied to electric decationizing apparatus 3 when the thermal power plant is not operating. The lever of second voltage V2 may be set to prevent the cations that are held by cation exchangers 39 from diffusing in deionization chamber 31 and to prevent the cations that have flowed into condensation chamber 33 from intruding into (returning to) deionization chamber 31 through cation exchange membrane 35, as shown in FIG. 2C. Second voltage V2 may be about the same level as first voltage V1, but no differences occur by setting the voltage too large (see Examples 1-1, 1-2). In addition, since water volume is reduced due to electrolysis of water and since thereby ion exchangers may be dried, it is preferable that second voltage V2 be as low as possible as long as the above condition is met. Second voltage V2 is, for example, 0.05V. By applying second voltage V2 of this level, it is possible to substantially prevent cations C in condensation chamber 33 from intruding into deionization chamber 31 through cation exchange membrane 35.

The timing when first voltage V1 may be shift to second voltage V2 is not limited, but, for example, it may be a time when the flow rate that is measured by flow meter 2 becomes zero. In this state, since there is no flow of water to be treated in deionization chamber 31, cations C are distributed in a region having a substantially constant width (the dimension in a direction perpendicular both to positive electrode 36 and to negative electrode 37) on the side of negative electrode 37 between the upstream end (the inlet) and the downstream end (the outlet) of deionization chamber 31. Specifically, the distribution of cations C at the outlet of deionization chamber 31 is not similar to FIG. 2A, where no cation is present, but cations C are present in a certain region on the side of negative electrode 37. However, as will be clear from the comparison between FIG. 2C and FIG. 2B, cations C are only present in a limited region at the outlet of deionization chamber 31. Therefore, when the thermal power plant restarts and the condensate water flows into deionization chamber 31 again, it takes only a short time to restore the state shown in FIG. 2A. It should be noted that valve 7 may be opened because the condensate water substantially does not flow into line 6 when the thermal power plant is not operating, but the valve may be closed in order to prevent the condensate water from accidentally flowing into the line.

Second voltage V2 may be continuously or intermittently applied when the thermal power plant is not operating, but it is not always necessary to do so. For example, it is possible to stop applying a voltage to electric decationizing apparatus 3 after the thermal power plant stops (this results in the state shown in FIG. 2B), and thereafter to apply second voltage V2 immediately before the thermal power plant restarts (this results in the state shown in FIG. 2C). In addition, if the measurement is not conducted by conductivity meter 4, then it is not necessary to apply second voltage V2 even after the thermal power plant starts. Second voltage V2 may be applied immediately before the measurement is conducted by conductivity meter 4. In other words, according to the present embodiment, it is sufficient to apply second voltage V2 that is lower than first voltage V1 to electric decationizing apparatus 3 that is charged with water to be treated before conductivity meter 4 starts measuring the conductivity of the decationized water.

In addition, when the application of a voltage to electric decationizing apparatus 3 stops, ion components that have moved to condensation chambers 32, 33 diffuse in deionization chamber 31. And, it is known that a weak reverse current flows between positive electrode 36 and negative electrode 37 in this state. Therefore, by limiting the reverse current, it is possible to prevent the ion components from diffusing from condensation chambers 32, 33 to deionization chamber 31, and water quality can be expected to improve quickly when the operation restarts. Therefore, by inserting an electronic element that limits the reverse current into a circuit that connects the DC power supply to positive electrode 36 and negative electrode 37, water quality can be improved quickly when the operation restarts. As an electronic element to limit the reverse current, for example, a semiconductor diode having a rectifying function may be used.

Second Embodiment

Figure 3:
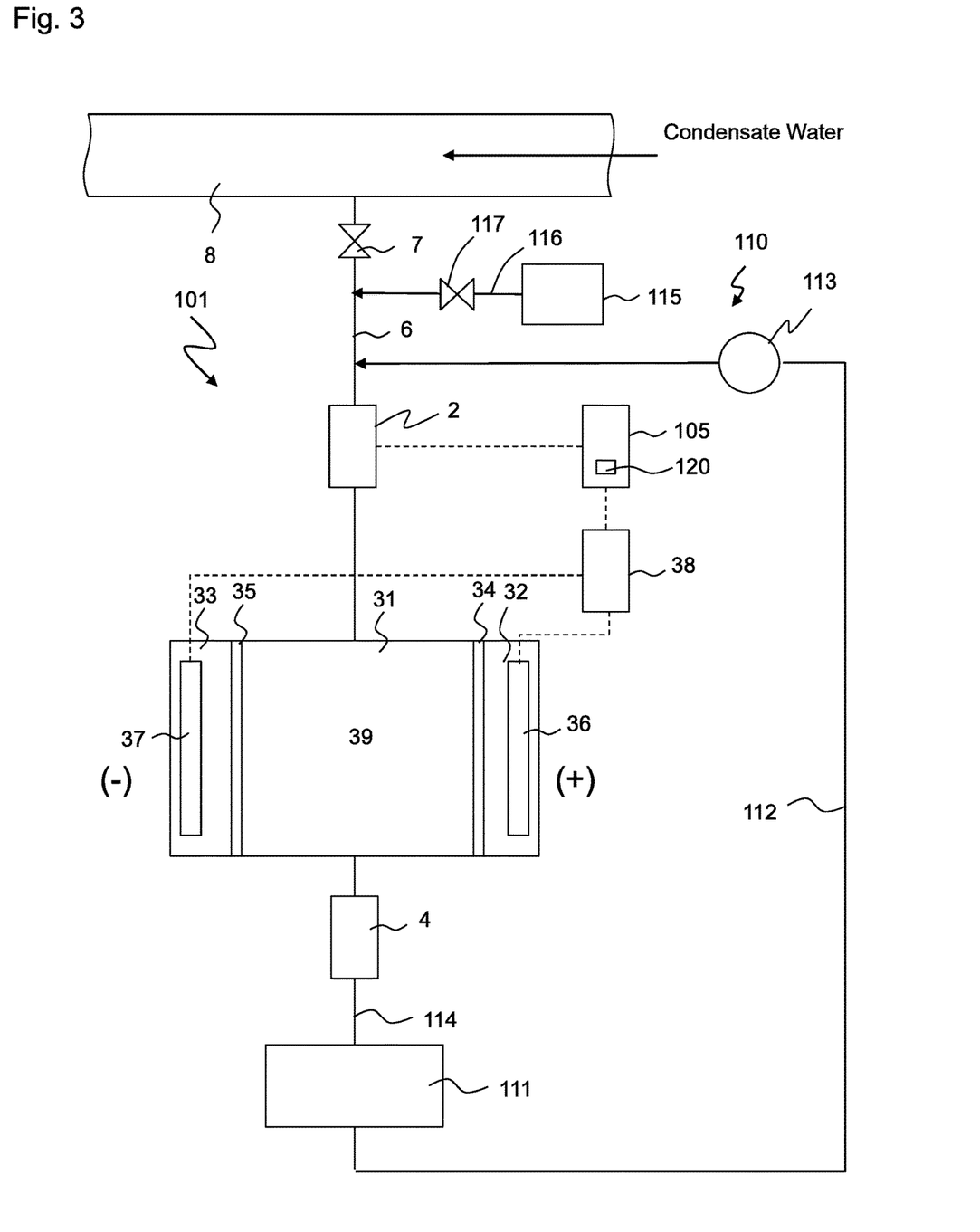
FIG. 3 is a conceptual view of a system for measuring the conductivity of decationized water according to the second embodiment of the present invention.

FIG. 3 shows a conceptual view of system for measuring the conductivity of decationized water 101 (hereinafter referred to as system 101) according to the second embodiment of the present invention. In the following description, differences from the first embodiment will be mainly described. Arrangements that are not explained are the same as those of the first embodiment.

System 101 of the present embodiment has water supply means 110 that supplies pure water to electric decationizing apparatus 3 before the thermal power plant stops or before electric decationizing apparatus 3 stops. Water supply means 110 has vessel 111 that stores pure water, water supply line 112 that connects vessel 111 to the inlet of electric decationizing apparatus 3 and transfer pump 113 that is provided on water supply line 112. The outlet of conductivity meter 4 is connected to vessel 111 via line 114, and the treated water that flows through line 114 is stored in vessel 111 without being discharged. Accordingly, the pure water is decationized water that is generated by electric decationizing apparatus 3. Water supply means 110 further has pure water source 115 that is connected to the inlet of electric decationizing apparatus 3 via lines 116, 6. A dedicated system may be provided as pure water source 115, but a pure water supply system of the thermal power plant may be used instead. Supply line 116 of pure water source 115 merges with line 6. Supply line 116 has valve 117. In this way, water supply means 110 has two separate water supply sources, but one of them may be omitted.

When the flow rate of the water to be treated that is measured by flow meter 2 becomes zero, control 105 activates transfer pump 113 or opens valve 117 in order to supply the pure water to electric decationizing apparatus 3. Valve 7 is closed in advance in order to prevent the pure water from flowing into condensate water line 8. Power supply 38 of electric decationizing apparatus 3 continues to provide current. Accordingly, a certain level of voltage continues to be applied between positive electrode 36 and negative electrode 37. Since no cation is newly supplied to electric decationizing apparatus 3, the cations that are present in deionization chamber 31 are gradually removed before the pure water is supplied, and the number of cations that stay in deionization chamber 31 is sufficiently reduced after a certain time. The time duration for supplying the pure water is selected such that the cations in deionization chamber 31 are sufficiently discharged, and it is, for example, 10-20 minutes. The amount of water that is supplied is preferably about 20 times as large as the volume of deionization chamber 31, and the effect is the same level even if pure water of 30 times or more is supplied. Control 105 has timer 120 that controls the time duration for supplying the pure water. Control 105 deactivates power supply 38 of electric decationizing apparatus 3 after a certain time for supplying the pure water passes. Most of the exchange groups of cation exchanger 39 are converted into $H^+$ form (that is, substantially no exchange group, such as in $NH_4^+$ form, is present), and deionization chamber 31 stays substantially free of cations.

Next, when the thermal power plant starts, electric decationizing apparatus 3 is also activated. Valve 7 is opened in order to supply condensate water from condensate water line 8 to electric decationizing apparatus 3. The pure water that is stored in deionization chamber 31 of electric decationizing apparatus 3 is discharged, and deionization chamber 31 is charged with condensate water. The pure water that filled deionization chamber 31 is not measured by conductivity meter 4 because it does not contain sea water components. Thereafter, condensate water is continuously supplied from condensate water line 8 to electric decationizing apparatus 3 and is treated by electric decationizing apparatus 3 before it is supplied to conductivity meter 4. The deionization chamber is put in the state shown in FIG. 2A after a certain time and is ready to measure conductivity. Since the transfer to this state is done only in a short time, measuring the conductivity can be immediately started.

Vessel 111 only need to have a capacity that corresponds to the amount of treated water (pure water) that is supplied, and any capacity larger than this is not required. After treated water of a required volume has been stored in vessel 111, vessel 111 may overflow with the water that is discharged from conductivity meter 4, or vessel 111 may be bypassed by a line (not shown) that bypasses vessel 111 in order to prevent the water from flowing in vessel 111.

According to the present embodiment, cations that stay in deionization chamber 31 of electric decationizing apparatus 3 are discharged while the pure water is supplied, and electric decationizing apparatus 3 stops thereafter. Thus, it is possible to limit cations that are contained in the water that is discharged from deionization chamber 31 after the thermal power plant restarts. As long as pure water is supplied before conductivity meter 4 begin measuring the conductivity of the decationized water and after the thermal power plant starts next time, the pure water may be supplied after the thermal power plant stops. It is preferable that the number of cations that are contained in water that is supplied to discharge the cations that have stayed in electric decationizing apparatus 3 be as small as possible, but cation concentration of the water may be lower than that of the water to be treated (low cation concentration water).

Third Embodiment

Figure 4:
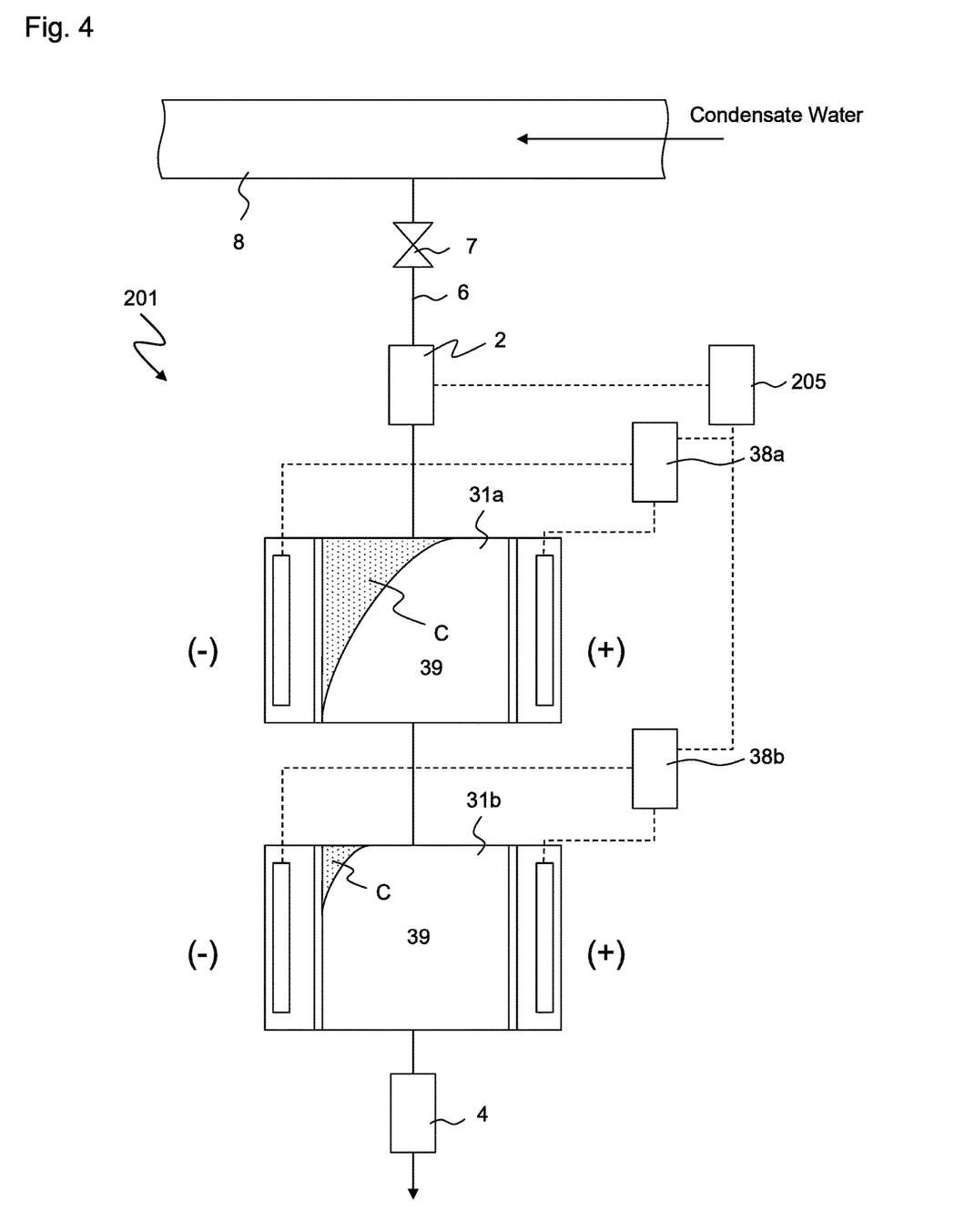
FIG. 4 is a conceptual view of a system for measuring the conductivity of decationized water according to the third embodiment of the present invention.

FIG. 4 shows a conceptual view of system for measuring the conductivity of decationized water 201 (hereinafter referred to as system 201) according to the third embodiment of the present invention. In the following description, differences from the first embodiment will be mainly described. Arrangements that are not explained are the same as those of the first embodiment.

System 201 of the present embodiment has first electric decationizing apparatus 3a and second electric decationizing apparatus 3b that are connected in series by a line. First electric decationizing apparatus 3a is located upstream of second electric decationizing apparatus 3b, and the water that is discharged from first electric decationizing apparatus 3a is supplied to second electric decationizing apparatus 3b in order to achieve two stage cation removal. First electric decationizing apparatus 3a and second electric decationizing apparatus 3b may have the same arrangement and the same dimensions. Since most of the cations are removed by first electric decationizing apparatus 3a, the distribution of cations C in deionization chamber 31 during operation is as shown in FIG. 4.

When the operation of the thermal power plant stops, power supply 38a of first electric decationizing apparatus 3a and power supply 38b of second electric decationizing apparatus 3b are also deactivated. Accordingly, as shown in FIG. 2B, cations are distributed in the entire region of deionization chambers 31 of first and second electric decationizing apparatuses 3a, 3b. However, since most of the cations are removed by first electric decationizing apparatus 3a, the number of cations that flow into second electric decationizing apparatus 3b is limited. Therefore, when the thermal power plant restarts, the number of cations that are discharged from second electric decationizing apparatus 3b is limited to a level such that there is only a small number of cations to allow conductivity meter 4 to sufficiently accurately measure the conductivity based on anions. Immediately after first electric decationizing apparatus 3a restarts, a larger number of cations C than the normal level flow from first electric decationizing apparatus 3a to second electric decationizing apparatus 3b, but since the cations are removed by second electric decationizing apparatus 3b, the measurement of the conductivity is not largely affected. It should be noted that the number of electric decationizing apparatuses 3 that are connected in series is not limited to two, and any number of electric decationizing apparatuses 3 may be connected in series. Conductivity meter 4 is connected to the outlet of the most downstream electric decationizing apparatus, and the conductivity of the decationized water that is discharged from the most downstream electric decationizing apparatus is measured by conductivity meter 4.

EXAMPLE

Water to be treated that contains ammonia at 1 mg/L was decationized by an EDI for ten hours, and the EDI was not operating for fifty hours. The EDI restarted, and water to be treated that contains ammonia at 1 mg/L was supplied at a flow rate of 10 L/h, and the time until the indication of the conductivity meter fell below 0.1 µS/cm was measured. The voltage that was applied to the EDI was 0.8V unless otherwise mentioned. The results were shown in Table 1. Examples 1-1, 1-2 correspond to the first embodiment, Example 2 correspond to the second embodiment, and Example 3 correspond to the third embodiment. In each Example, the time until the indication of the conductivity meter fell below 0.1 µS/cm was shortened, as compared to the comparative example.

TABLE 1

| | Content | Time until the conductivity fell below 0.1 µS/cm |
|---|---|---|
| Comparative example | No countermeasure | 6 min. |
| Example 1-1 | A voltage of 0.05 V was continuously applied to the EDI during stoppage | <0.5 min. |
| Example 1-2 | A voltage of 0.1 V was continuously applied to the EDI during stoppage | <0.5 min. |
| Example 2 | Pure water is supplied to the EDI before stoppage | <0.5 min. |
| Example 3 | Two stage EDIs are employed | 1.5 min. |

Although some preferred embodiments of the present invention have been illustrated and described in detail, it should be appreciated that various changes and modifications can be made thereto without deviating from the spirit and the scope of the appended claims.

The invention claimed is:

1. A system for measuring conductivity of decationized water comprising:
a line that branches from a condensate water line;
an electric decationizing apparatus that is arranged on the line and that generates decationized water while applying a first voltage to condensate water that contains cations and anions, the electric decationizing apparatus including a positive electrode, a negative electrode, and a deionization chamber that is positioned between the positive electrode and the negative electrode;
a flow meter that is arranged on the line and that measures a flow rate of the condensate water that flows into the electric decationizing apparatus;
a conductivity meter that measures conductivity of the decationized water that is generated by the electric decationizing apparatus; and
a control to which an output signal of the flow meter is transmitted,
wherein, in a state in which the output signal indicates that flow of the condensate water stops, the control controls the electric decationizing apparatus such that before the first voltage is applied to the electric decationizing apparatus and before the conductivity meter begins measuring the conductivity of the decationized water, a second voltage that is one-eighth the first voltage or less is applied to the electric decationizing apparatus such that cations are unevenly distributed on a side of the negative electrode in the deionization chamber in a state in which the electric decationizing apparatus is charged with the condensate water.

2. A system for measuring conductivity of decationized water comprising:
   an electric decationizing apparatus that generates decationized water from water to be treated that contains cations and anions;
   a conductivity meter that measures conductivity of the decationized water that is generated by the electric decationizing apparatus;
   a water supplier, including at least a supply line, that is configured to supply low cation concentration water whose cation concentration is lower than that of the water to be treated to the electric decationizing apparatus; and
   a control that controls the water supply means such that before the decationized water is generated by the electric decationizing apparatus and before the conductivity meter begins measuring the conductivity of the decationized water, the low cation concentration water is fed to the electric decationizing apparatus while a voltage is applied to the electric decationizing apparatus, wherein
   the electric decationizing apparatus includes a deionization chamber, the low cation concentration water is fed to the electric decationizing apparatus such that the deionization chamber is substantially free of cations, as determined by a conductivity value of less than 0.1 $\mu$S/cm, and the control deactivates the electric decationizing apparatus after the low cation concentration water is fed.

3. The system for measuring conductivity of decationized water according to claim 2, wherein the water supplier further comprises:
   a vessel that stores the decationized water as the low cation concentration water; wherein the decationized water is generated by the electric decationizing apparatus;
   the water supply line that connects the vessel to an inlet of the electric decationizing apparatus and;
   a transfer pump that is provided on the water supply line,
   and wherein the control comprises a timer that controls time duration for feeding the low cation concentration water to the electric decationizing apparatus.

4. The system for measuring conductivity of decationized water according to claim 1, wherein the water to be treated is the condensate water of a thermal power plant.

5. The system for measuring conductivity of decationized water according to claim 2, wherein the water to be treated is condensate water of a thermal power plant.

* * * * *